US00PP36701P2

(12) United States Plant Patent
Chen et al.

(10) Patent No.: US PP36,701 P2
(45) Date of Patent: May 20, 2025

(54) ***EPIPREMNUM* PLANT NAMED 'UF-Ea-0314'**

(50) Latin Name: *Epipremnum aureum.*
Varietal Denomination: UF-Ea-0314

(71) Applicant: Florida Foundation Seed Producers, Inc., Marianna, FL (US)

(72) Inventors: Jianjun Chen, Lake Mary, FL (US); Richard J. Henny, Tavares, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/968,358

(22) Filed: Dec. 4, 2024

Related U.S. Application Data

(60) Provisional application No. 63/550,135, filed on Feb. 6, 2024.

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
See application file for complete search history.

(56) References Cited

U.S. PATENT DOCUMENTS

PP20,457 P2 * 11/2009 Bryant ..... Plt./373
PP35,450 P2 * 10/2023 Vikos ..... A01H 6/00 Plt./373
PP36,475 P2 * 2/2025 Kap ..... Plt./373

* cited by examiner

*Primary Examiner* — Karen M Redden
(74) *Attorney, Agent, or Firm* — James R. Holm

(57) ABSTRACT

A new and distinct cultivar of Pothos (*Epipremnun aureum*) plant named 'UF-Ea-0314', particularly distinguished by medium to large sized plants, narrow and falcate shaped leaves, and stable solid green leaf coloration that has been maintained over more than 20 generations of asexual propagation without any variation.

5 Drawing Sheets

Genus and species: *Epipremnum aureum.*
Cultivar denomination: 'UF-Ea-0314'.

ACKNOWLEDGEMENT OF FEDERAL RESEARCH SUPPORT

N/A.

BACKGROUND OF THE NEW CULTIVAR

*Epipremnum* Schott, commonly known as Pothos, belongs in the family Araceae and is native to the southeast Asian and Solomon Islands in the Pacific. *Epipremnum* has about 10 species, but only *E. aureum* or *E. pinnatum* 'Aureum' (Boyce, 1998) has been widely grown as an ornamental and is among the most popular foliage plants worldwide. Pothos is an important foliage plant in the commercial trade. Based on the USDA Floriculture Crops Statistics, the wholesale value of Pothos in 2018 was $22.89 million. It ranked as the third among all cultivated foliage plant genera. With the increased popularity of "living walls" since 2010, Pothos has been the highest in-demand indoor foliage plant, especially demand for cultivars with contrasting and bright foliage colors. Prior to 2009, there have been only four cultivars available in commercial trade, 'Golden Pothos' (unpatented), 'Marble Queen' (unpatented), 'Jade' (unpatented), and 'Neon' (unpatented). In 2009, two new Pothos cultivars were released by the University of Florida, 'UFM10' (U.S. Plant Pat. No. 20,930, commercial name Green Genie™) and 'UFM12' (U.S. Plant Pat. No. 21,217, commercial name Pearls and Jade™). These two cultivars are the result of mutation breeding through exposure to gamma ray radiation. In 2022, three new Pothos cultivars were released by the University of Florida, 'UF-Ea-0311' (U.S. Plant Pat. No. 35,875), 'UF-Ea-0316' (U.S. Plant Pat. No. 35,876), and 'UF-Ea-0317 (U.S. Plant Pat. No. 35,874) '. These Pothos cultivars were developed through direct in-vitro somatic cell embryogenesis from leaf explants.

Pothos has bisexual flowers like its relatives *Anthurium* and *Spathiphyllum* but rarely flowers in nature. Prior to the present disclosure, there have been no literature reports of Pothos breeding through hybridization. Gibberellic acid ($GA_3$) is known to stimulate flowering in many flowering plant species. Molecular analysis has shown that transcripts for the biosynthesis of $GA_3$, EaGA3oxl and $GA_3$-responsive floral meristem gene, EaLFY were inactive in Pothos. Thus, exogenous application of $GA_3$ has shown to induce Pothos flowering. After the induction of flowering, pollen can be collected and transferred to the stigmas of the same flower (self-pollination) or to that of a different flower (cross-pollination) to produce seed.

SUMMARY OF THE INVENTION

The invention relates to a new and distinct cultivar of Pothos plant named 'UF-Ea-0314'. In March 2012, 'UF-Ea-0314' was isolated from in-vitro regenerated populations of 'UF-Ea-0310' (U.S. plant patent application Ser. No. 18/955,115). Variegated leaves of 'UF-Ea-0310' were dissected into variegated, white, and green sections. The sections were cut into approximately 1 $cm^2$ pieces and placed on MS medium (Murashige and Skoog, 1962) supplemented with 8.0 μM CPPU and 1 μM NAA. Somatic embryos directly occurred on the leaf surfaces and cut ends in 4-6 weeks. Embryo conversion took place in the next 4-6 weeks. Plantlets induced from green and variegated explants mainly had green leaves. Plantlets induced from the white explants were largely green, accounting for about 80%, while about 20% of them were entirely white. Both green and white plantlets were selected and transplanted into plug trays filled with a substrate and placed in a shaded greenhouse for acclimatization. Green plants survived, while white plants died. The green-leaved plants were potted in 15-cm pots for evaluation. All green-leaved plants have remained green without variegation since their identification in March 2012. 'UF-Ea-0314' was selected in August 2012 from said regenerated population of green-leaved plants based on leaf shape, growth vigor, and leaf color stability.

First asexual propagation of 'UF-Ea-0314' through single or double eye stem or vine cuttings occurred in Apopka, Florida in October 2012; since then, it has been asexually propagated through single or double eye stem or vine cuttings for 20 or more generations without any variation.

Plant Breeder's Rights for the new cultivar 'UF-Ea-0314' have not been applied for, and 'UF-Ea-0314' has not been made publicly available more than one year prior to the filing date of this application.

The new cultivar 'UF-Ea-0314' has not been observed under all possible environmental conditions. The phenotype of the new cultivar may vary with variations in environment and cultural practices such as temperature, light intensity, fertilization, irrigation, and application of plant growth regulators without any change in genotype.

The following are the most outstanding and distinguishing characteristics of 'UF-Ea-0314' when grown under normal horticultural practices in Apopka, Florida: medium to large sized plants, narrow and falcate shaped leaves with a smaller leaf area compared to the parent Pothos plant 'UF-Ea-0310' and the commercial unpatented green Pothos cultivar 'Jade'. Additionally, 'UF-Ea-0310' has stable solid green leaf coloration that has been maintained over more than 20 generations of asexual propagation without any variation.

DESCRIPTION OF THE FIGURES

This new Pothos cultivar 'UF-Ea-0314' is illustrated by the accompanying photographs, which show the plant's form and foliage. The colors shown are as true as can be reasonably obtained by conventional photographic procedures. The photographs are of six-month-old plants grown from unrooted cuttings in November 2018 in a shaded greenhouse in Apopka, Florida.

DETAILED BOTANICAL DESCRIPTION OF THE CULTIVAR

Figure 1:
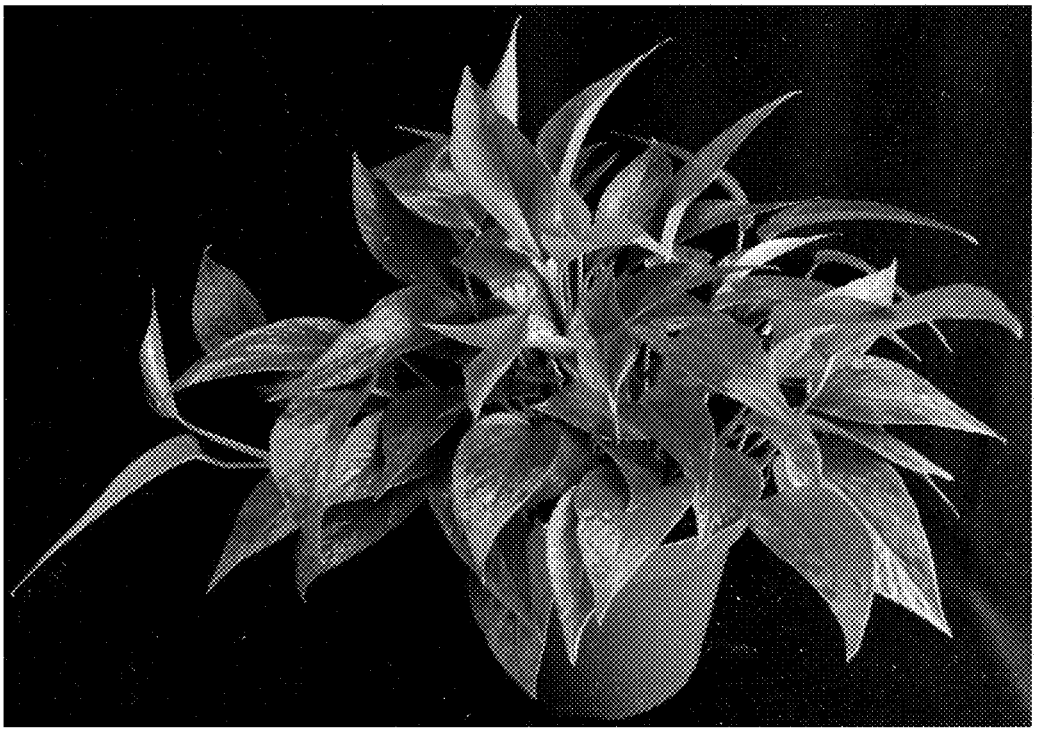
FIG. 1 shows the growth habit, form, and foliage of the new Pothos cultivar 'UF-Ea-0314'.
Figure 2:
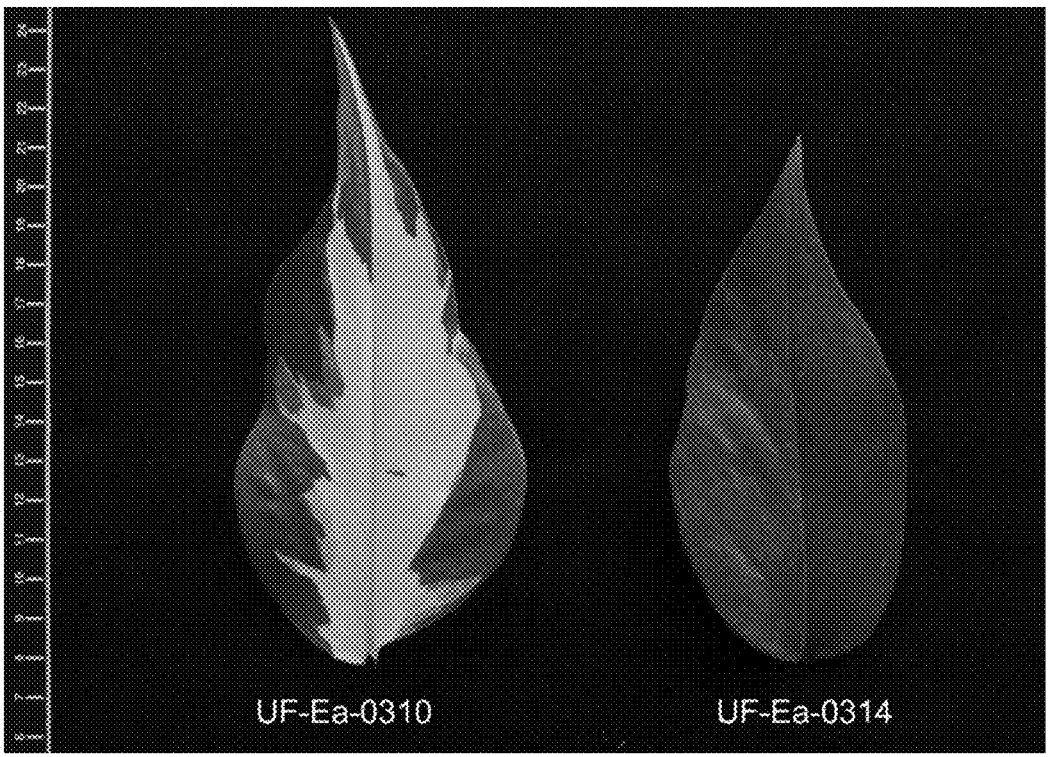
FIG. 2 shows a side-by-side comparison of the adaxial surface of a leaf of 'UF-Ea-0314' (right) and 'UF-Ea-0310' (left)
Figure 3:
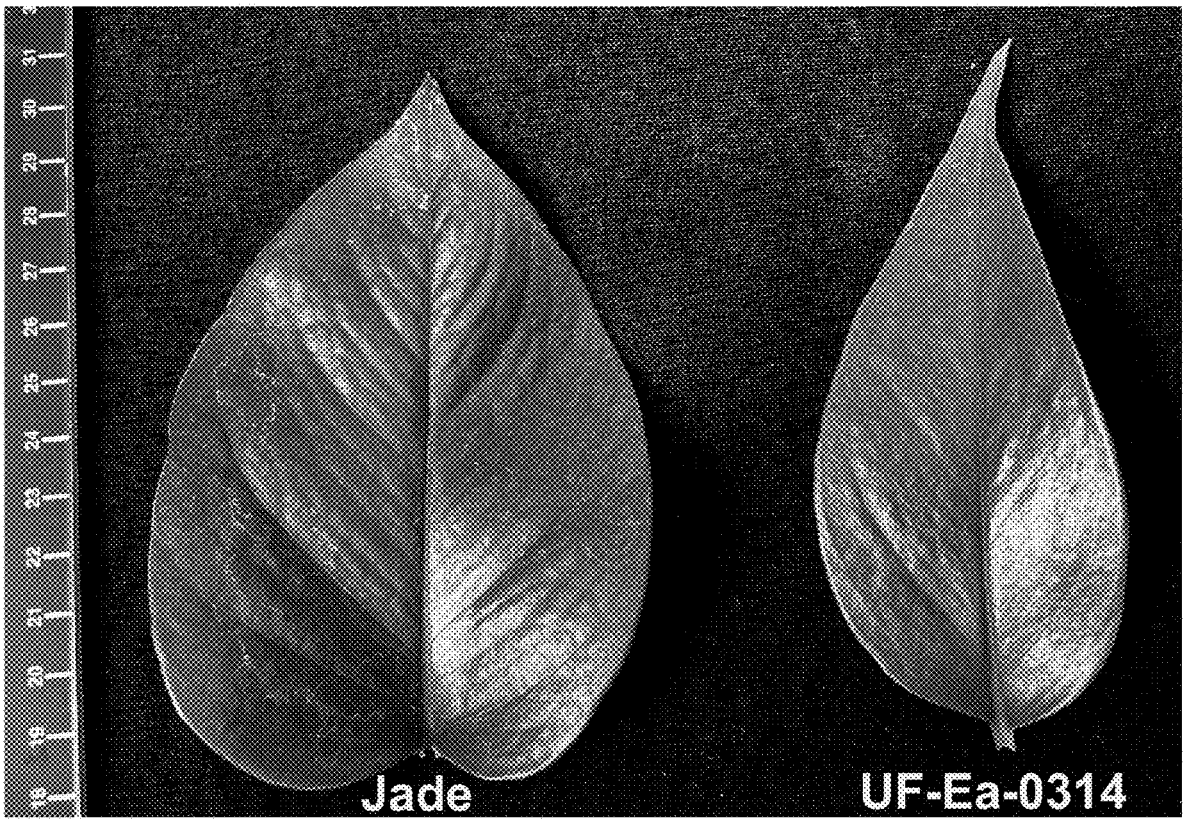
FIG. 3 shows a side-by-side comparison of the adaxial surface of a leaf of 'UF-Ea-0314' (right) and the commercial unpatented green Pothos cultivar 'Jade' (left)
Figure 4:
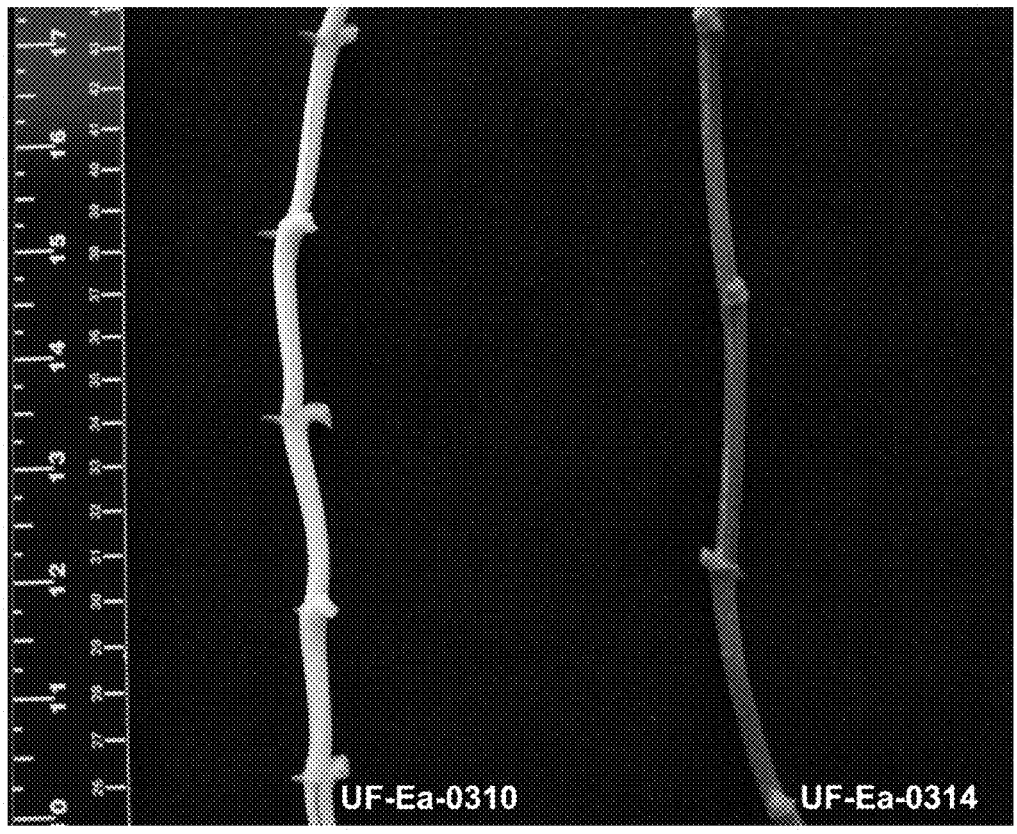
FIG. 4 shows a side-by-side comparison of a stem of 'UF-Ea-0314' (right) and 'UF-Ea-0310' (left)
Figure 5:
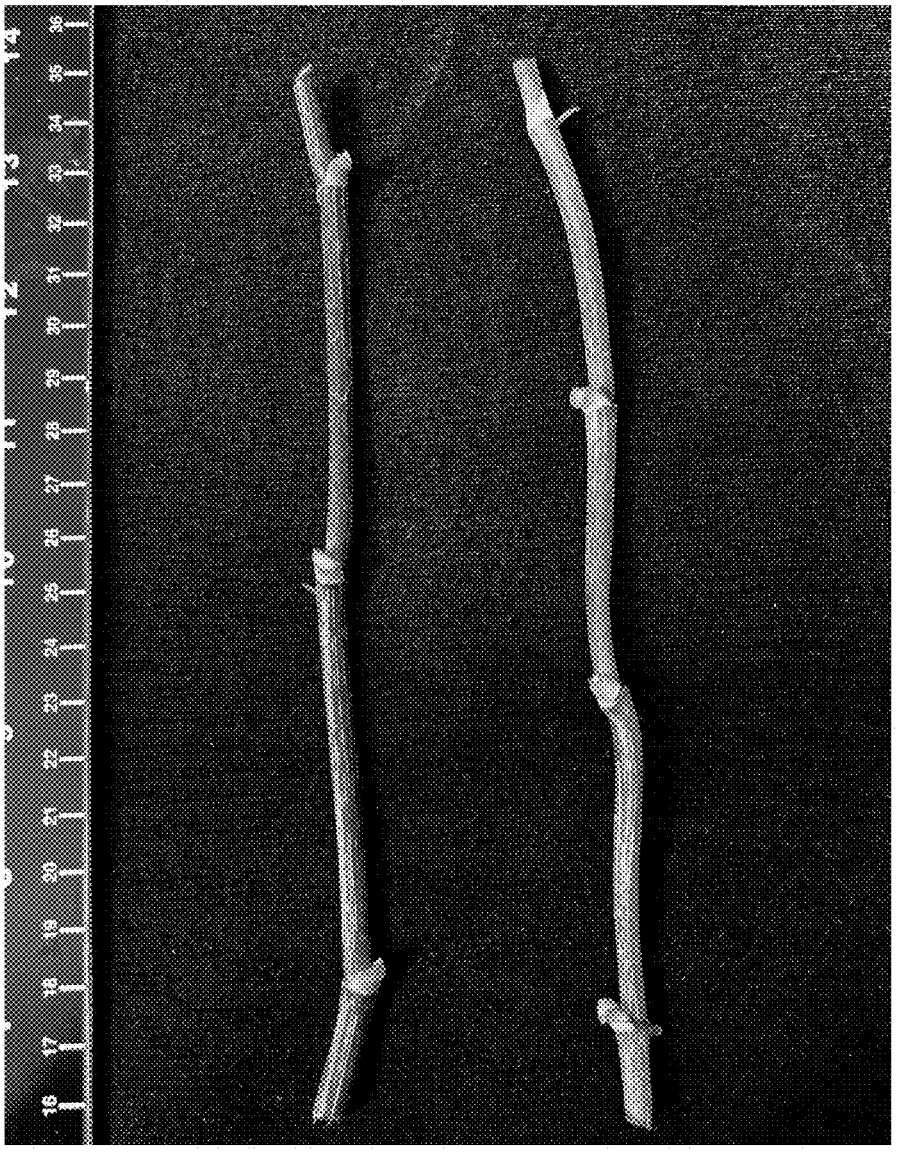
FIG. 5 shows a side-by-side comparison of a stem of 'UF-Ea-0314' (right) and the commercial unpatented green Pothos cultivar 'Jade' (left).

Foliage color was determined under full sun conditions in the middle of the day in a shaded greenhouse with 75% light exclusion. Color references are to The R.H.S. Colour Chart of The Royal Horticultural Society of London (R.H.S.), 1995 Edition. The following detailed description of 'UF-Ea-0314' was obtained using six-month-old plants grown from unrooted cuttings in May 2018 in a shaded greenhouse in Apopka, Florida. The plants were propagated in mist for 21 days after the cuttings were planted in soil, then grown in 15 or 20 cm diameter pots with approximately 15 cuttings per pot for approximately 3-4 additional weeks.

BOTANICAL DESCRIPTION

Botanical classification:

*Family*.—Araceae.

*Botanical name*.—*Epipremnum aureum*.

*Common name*.—Pothos.

*Cultivar*.—'UF-Ea-0314'.

Plant description:

*Plant type*.—Perennial tropical vine.

*Growth habit*.—Compact or vining.

*Height from soil level to top of foliar plane*.—Approximately 20 cm.

*Growth vigor*.—Moderate (average of 0.4 cm per day of vine growth during the summer months in Apopka, Florida).

*Branching characteristics*.—One main stem (vine), no lateral branching.

*Vine length*.—Approximately 35.0 cm on a 3-month-old stem.

*Vine diameter*.—Approximately 0.5 cm.

*Internode length*.—6.4 cm.

*Texture of vines*.—Glabrous with some raised linear striations on the upper side.

*Shape of vines*.—Round.

*Color of vines*.—Upper sides exposed to light are green (131B) while the under sides facing away from light are light green (129D).

*Number of internodes and leaves per vine*.—6 to 8 on a 3-month-old vine.

Propagation:

*Type of cuttings*.—Vegetative stem cuttings having at least 1 node.

*Time to initiate roots*.—21 days.

*Time to produce a rooted cutting*.—20 weeks after root establishment.

*Root habit*.—One aerial root oriented downwards and present at each basal node, aerial roots produce fine roots when in contact with the soil.

*Root description*.—Aerial roots are 1-5 cm in length and 1-2 mm in diameter, colored brown (165A); soil main roots are about 1-2 mm in diameter and fine roots are about 0.4 mm in diameter and colored white (NN155D).

Foliage description:

*Arrangement*.—Alternate.

*Attachment*.—Petiolate.

*Leaf*.—Shape: Falcate. Length: 14.2 cm. Width: About 5.5 cm. Leaf area: 48.6 $cm^2$. Apex shape: Acute to slightly acuminate. Base shape: Truncate to slightly cordate. Texture (both upper and lower surfaces): Glabrous and leathery. Orientation: Newer leaves are held slightly upwards, mature leaves are held horizontally. Margins: Entire. Color: Upper surface: Green (135A). Lower surface: Green (138A). Leaf sheen (both upper and lower surfaces): Shiny. Venation: Pattern: Eucamptodromous. Color: Upper surface: Green (137A). Lower surface: Green (137D).

*Petiole*.—Length: 10 cm. Width: 0.3 cm. Color: Green (131B).

Inflorescence: None observed to date.

Fruit and seed set: None observed to date.

Disease and insect resistance: None observed to date.

Cold tolerance: Tolerant down to 5° C.

Drought tolerance: Tolerant.

COMPARISON WITH PARENT VARIETY AND COMMERCIAL VARIETY

Plants of the new cultivar 'UF-Ea-0314' may be distinguished from its parent variety 'UF-Ea-0310' and the unpatented commercial variety 'Jade' by characteristics described in Table 1.

TABLE 1

| Cultivar | Leaf shape | Leaf color | Length of largest leaf (cm) | Width of largest leaf (cm) | Leaf area ($cm^2$) |
|---|---|---|---|---|---|
| 'UF-Ea-0310' | Acuminate | White, grey, and green in irregular spots | 14.5 a[w] | 6.7 b | 66.7 b |
| 'UF-Ea-0314' | Falcate | Green | 14.2 a | 5.5 c | 48.6 c |
| 'Jade' | Aristate | Green | 12.8 a | 8.4 a | 80.6 a |

| Cultivar | Stem color | Internode length (cm) | Growth habit | Growth vigor[y] | Quality rating[x] |
|---|---|---|---|---|---|
| 'UF-Ea-0310' | Light yellow | 4.2 c | Compact | 2.5 a | 4.8 a |
| 'UF-Ea-0314' | Green | 6.4 b | Compact or vining | 3.0 a | 4.5 a |
| 'Jade' | Green | 8.1 a | Compact or vining | 3.0 a | 3.5 b |

[z]Data are means of a three-year evaluation (2018, 2019, and 2020).

[y]Growth vigor rating: 1 = extremely slow, 2 = slow, 3 = moderate, and 4 = fast.

[x]Quality rating was based on a scale of 1 to 5: with 1 = unacceptable; 2 = substandard, not saleable; 3 = good, saleable; 4 = very good, attractive; and 5 = excellent, very attractive. The grading was conducted on 11 Nov. 2018 and given by 74 participants.

[w]Different letters within a column indicate significance at $P < 0.05$ level based on the LSD analysis.

What is claimed is:

1. A new and distinct *Epipremnum* plant named 'UF-Ea-0314' as illustrated and described herein.

* * * * *